(12) United States Patent
Cho et al.

(10) Patent No.: US 10,201,578 B2
(45) Date of Patent: Feb. 12, 2019

(54) **PHARMACEUTICAL COMPOSITION OR HEALTH FOOD COMPRISING *LONICERA CAERULEA* VAR. *EDULIS* FRUIT EXTRACTS AS ACTIVE INGREDIENTS FOR PREVENTING OR IMPROVING ISCHEMIC CEREBROVASCULAR DISEASES**

(71) Applicant: University-Industry Cooperation Group Of Kyung Hee University, Gyeonggi-do (KR)

(72) Inventors: Seung Hun Cho, Seoul (KR); Won Ki Kim, Seoul (KR); Jae Chul Lee, Seoul (KR)

(73) Assignee: University-Industry Cooperation Group of Kyung Hee University (KR)

( * ) Notice: Subject to any disclaimer, the term of this patent is extended or adjusted under 35 U.S.C. 154(b) by 653 days.

(21) Appl. No.: 14/386,221

(22) PCT Filed: Mar. 19, 2013

(86) PCT No.: PCT/KR2013/002257
§ 371 (c)(1),
(2) Date: Dec. 18, 2014

(87) PCT Pub. No.: WO2013/141581
PCT Pub. Date: Sep. 26, 2013

(65) Prior Publication Data
US 2015/0125561 A1    May 7, 2015

(30) Foreign Application Priority Data
Mar. 19, 2012 (KR) .......................... 10-2012-0027697

(51) Int. Cl.
A61K 36/355    (2006.01)
(52) U.S. Cl.
CPC ................................. A61K 36/355 (2013.01)
(58) Field of Classification Search
None
See application file for complete search history.

(56) References Cited

U.S. PATENT DOCUMENTS

2011/0123639 A1    5/2011  Chan et al.

FOREIGN PATENT DOCUMENTS

KR    10-2007-0026284 A    3/2007
KR       1020070026284 A    3/2007

OTHER PUBLICATIONS

Chaovanalikit, A. et al., "Characterization and quantification of anthocyanins and polyphenolics in blue honeysuckle (*Lonicera caerulea* L)", Journal of Agricultural and Food Chemistry, 2004, vol. 52, pp. 848-852.
Kang, T.H. et al., "Neuroprotective effects of the cyanidin-3-O-b-D-glucopyranoside isolated from mulberry fruit against cerebral ischemia", Neuroscience Letters, 2006, vol. 391, pp. 168-172.
Jurikova, T. et al., "Phenolic profile of edible honeysuckle berries (genus *Lonicera*) and their biological effects", Molecules, Dec. 22, 2011, vol. 17, pp. 61-79.
Svarcova, I. et al., "Berry fruits as a source of biologically active compounds: the case of Lonicera caerules", Biomed Pap Med Fac Univ Palacky Olomouc Czech Republic, 2007, vol. 151, No. 2, pp. 163-174.
International Search Report, PCT/KR2013/002257, dated Jul. 9, 2013.
Kihwan Moon, International Preliminary Report on Patentability and Written Opinion, PCT/KR2013/002257, dated Oct. 2, 2014.
Chaovanalikit et al. "Characterization and quantification of anthocyanins and polyphenolics in blue honeysuckle (*Lonicera caerulea* L.)," Journal of Agricultural and Food Chemistry. 2004, vol. 52, pp. 848-852.
Jurikova et al., "Phenolic profile of edible honeysickle berries (genus *Lonicera*) and their biological effects," Molecules, Dec. 22, 2011, vol. 17, pp. 61-79.
Kang et al., "Neuroprotective effects of the cyanidin-3-O-β-D-glucopyranoside isolated from mulberry fruit against cerebral ischemia," Neuroscience Letters, 2006, vol. 391, pp. 168-172.
Svarcova et al., "Berry fruits as a source of biologically active compounds: the case of *Lonicera caerulea*," Biomed Pap Med Fac Univ Palacky Olomouc Czech Repub. 2007, Vo. 151, No. 2, pp. 163-174.

*Primary Examiner* — Aaron J Kosar
(74) *Attorney, Agent, or Firm* — Gavrilovich, Dodd & Lindsey LLP

(57) ABSTRACT

The present invention relates to a composition containing a fruit extract of *Lonicera caerulea* L. var. *edulis* as an active ingredient for the prevention and treatment of ischemic cerebrovascular disease. The fruit extract of *Lonicera caerulea* L. var. *edulis* according to the present invention has a nerve cell-protecting effect, thereby remarkably reducing neurobehavioral impairments and infarct volume due to ischemic cerebrovascular disease. Therefore, it can be provided as a pharmaceutical composition for the prevention or treatment of ischemic cerebrovascular disease, and as a health food for the prevention or improvement of ischemic cerebrovascular disease.

2 Claims, 3 Drawing Sheets

PHARMACEUTICAL COMPOSITION OR HEALTH FOOD COMPRISING *LONICERA CAERULEA* VAR. *EDULIS* FRUIT EXTRACTS AS ACTIVE INGREDIENTS FOR PREVENTING OR IMPROVING ISCHEMIC CEREBROVASCULAR DISEASES

CROSS REFERENCE TO RELATED APPLICATIONS

This application is a U.S. National Stage Application filed under 35 U.S.C. 371 and claims priority to International Application No. PCT/KR2013/002257, filed Mar. 19, 2013, which application claims priority to Korean Application No. 10-2012-0027697, filed Mar. 19, 2012, the disclosures of which are incorporated herein by reference in their entirety.

BACKGROUND OF THE INVENTION

1. Field of the Invention

The present invention relates to a pharmaceutical composition or a health food containing a fruit extract of *Lonicera caerulea* L. var. *edulis* as an active ingredient for prevention and treatment of ischemic cerebrovascular disease.

2. Description of the Related Art

According to WHO estimates, 17 million people die of vascular disease each year, and vascular disease is the first leading cause of death, accounting for one-third of all deaths. In the U.S., vascular disease ranks as the first leading cause of death among adults aged 65 or older, and the second leading cause of death following cancer among adults aged from 45 to 64. With the growing aging population, deaths due to vascular disease are projected to increase. In South Korea, cancer is the first leading cause of death, followed by cerebrovascular disease and heart disease in that order. The number of patients with the blood circulatory diseases, being ranked as the second and third causes of death, has rabidly increased recently by 7 times, compared to the early 1980s.

Stroke is commonly known as 'cerebrovascular accident', and refers to a focal neurological impairment such as loss of consciousness, hemiplegia, dysarthria, which is caused by any sudden interruption in blood supply to the brain affected due to the occlusion or rupture of cerebral blood vessels. Stroke is largely divided into ischemic stroke and hemorrhagic stroke. Ischemic stroke is caused by ischemia of brain tissues due to reduction or interruption of blood supply to brain tissues, and hemorrhagic stroke is caused by bleeding in brain tissues due to a rupture of blood vessels. That is, depending on the cause, it is divided into cerebral infarction caused by blockage of cerebral blood vessel and cerebral hemorrhage caused by rupture of cerebral blood vessels, and cerebral hemorrhage is further divided into intracerebral hemorrhage and subarachnoid hemorrhage (SAH) due to rupture of cerebral aneurysm resulting from a balloon-like deformation of cerebral blood vessels. Further, cerebral infarction is divided into cerebral thrombosis (obstruction of blood vessels due to the formation of a blood clot within the cerebral blood vessels) and cerebral embolism (obstruction of a cerebral artery caused by thrombus or blood clot due to heart disorders, which was traveled to the brain). Because stroke can occur anywhere in the brain, it can cause impairments of all body functions. Further, brain injury generated is determined by severity and location of the injury itself, and severe brain injury due to stroke causes disturbances in movement and sensation, and inhibits higher functions such as memory, learning, calculation, and reasoning, etc., and also causes severe aftereffects such as stroke, weak intelligence, learning disability, epilepsy, etc. Even after stroke recovery, associated sequelae still remains in most cases, thus causing as much as 7 billion US dollars of social and economic losses each year (Davenport et al. Journal of Neurology, 2000, vol. 68, p. 277).

Ischemic brain injury depends on blood circulation. When there is a disorder in normal cerebral blood flow (50 ml/gram/minute) caused by several pathological conditions in blood vessels supplying blood to the brain, transient cerebral ischemia rapidly develops into complete stroke, leading to death. Because ischemic stroke occurs suddenly, being accompanied by neurological disorders, and progresses further within a short time, its complete treatment is impossible even with emergent thrombolytic therapy. Even if it may not lead to an immediate death, its side effects and sequelae are still so serious directly or indirectly causing social and economic losses. Accordingly, its prevention is very important.

Prevention of ischemic stroke is divided into primary prevention for removing risk factors that cause changes in blood flow such as increase in serum cholesterol level, hypertension, heart diseases, etc., and secondary prevention for preventing further aggravation after the onset of ischemic stroke. Previous studies regarding foods capable of preventing ischemic stroke have focused on reducing injuries due to particular risk factors. In particular, when brain ischemia caused by reduced blood supply to the brain occurs, the opening of calcium ion channels by glutamate leads to excessive influx of Ca ions thus causing excitotoxicity, or destroying enzyme groups in nerve cells by oxygen radicals produced via reperfusion. Target-specific studies regarding the mechanism of the neuron damage are still not satisfactory, requiring further progress in the related studies (Hagberg H et al., Neurosci Lett. 78:311-317, 1987).

In recent years, international studies have reported that food components such as carnosine, ellagic acid derivatives, carotene derivatives, S-cysteinyl derivatives influence primary and secondary prevention of ischemic brain injury. As therapeutic agents for stroke, glutamate receptor blockers for the prevention of primary (acute) brain injury, and therapeutic agent using antioxidants have been developed. However, the studies have not been successful due to lack of efficacy or toxicity problems observed during clinical trials. NMDA receptor antagonists have not been used because of severe toxicities, and most of them failed to pass clinical tests.

There have been no sufficient target-specific studies both home and abroad to elucidate the correlation between food components and the mechanisms of neuronal damage. Furthermore, there are few successful cases which have confirmed the effects of food components in animals' brains and successfully developed products therefrom. In fact, most studies in South Korea have been conducted at the level of experimental assays, and more sophisticated studies such as functional materials, mechanisms underlying in vivo physiological activities, platform technologies for modification of materials have not been well performed.

Most functional materials currently available in South Korea are simple complex type, and some of functional foods have low usefulness because of oxidation and browning due to exposure to oxygen and they also have a low-grade appearance as food materials. Thus, there is a need for the development of a basic technique capable of forming a blocking film by coating to secure storage stability and maintain activities of active ingredients, and a processing technique capable of applying active materials to proper food vehicles to improve availability. However, the efforts have not been successful yet.

To date, most drugs that have been developed as such are glutamate receptor antagonists, antioxidants, calcium or sodium ion channel blockers, etc., and effective drugs have not been developed yet. Therefore, there is a need to employ breakthrough ideas and a new concept for the accomplishment of target-specific drug discovery.

Meanwhile, reportedly, inflammatory reactions occur in the central nervous system, thus becoming one of the major causes of neuronal degeneration. Thus, the inflammatory reactions appearing after the occurrence of the brain ischemic stroke will become a target for the development of a novel therapeutic agent for stroke. Such therapeutic agent are expected to be comprised of the medicines either to suppress the enzyme activity involved in the separation of cytotoxic substances or to suppress the deposition of neutrophils (Dirnagl, U. et al; TINS., 22, pp 391-397, 1999).

Hewett et al. discovered that activated glial cells may affect death of nerve cells (Hewett, S. J. et al: Neuron, 13:487-494 1994; Hewett, S. J. et al, Stroke, 27:1586-15911996). Activated glial cells increase production of inflammatory factor, cytokine such as TNF-alpha, interleukin which can cause cytotoxicity, thereby increasing cytotoxicity on nerve cells and glial cells.

Inflammatory molecules secreted from macrophage and microglia, and death of nerve cells thereby are important, and in particular, control of glial cell activation and protection of nerve cells are the main targets for the prevention and control of stroke and development of therapy.

The efforts to develop novel crops for a special purpose using plants have enabled their annual production increase, but their utilization has been low for being used as general additives through a simple process such as an oil extraction process, or added to oriental medicines in the form of extracts. However, because plants are highly expected to contain active substances showing prophylactic activity against ischemic stroke, and several plants have been traditionally used for the prevention of stroke in the oriental medicine, development of plants as health food materials is expected to render an added value on the plants. Accordingly, there is a need for a systematic approach to develop functional health foods by developing a technology capable of screening food materials for preventing ischemic stroke from domestic plants, investigating their efficacy in animal tests, and then applying them to functional foods.

*Lonicera caerulea L.* var. *edulis* is a dicotyledonous plant belonging to the Family Caprifoliaceae of the Order Rubiales. It is a deciduous shrub growing to 1.5 m in height, densely branched, and has shield-shaped bracts at nodes of twigs. The inner part of branches is white. The leaves are opposite, lanciform or elliptic and blunt- or sharp-ended, lack teeth on the margins, have short hairs on the margins and surface, and have many wooly hairs underneath. The flowers usually have short stalks, which arise from leaf axils, have funnel-shaped creamy white corollas, and bloom in summer. Each calyx has five toothed sepals. The corollas are yellowish white, cylindrical campanulate, 1.2-1.5 cm long, and slightly hairy. The stamens are shorter than styles and have no hairs, and the two ovaries are fused together. The fruits are oval or nearly circular, ripen to purplish black between July and October, and are covered with white powder. This shrub is an arctic plant that is widespread in Siberia, Sakhalin, the Northern region of China, Tibet, North Korea, and the like.

At present, as the inventions regarding the use of *Lonicera caerulea L.* var. *edulis* extract, Korean Patent No. 10-0699790 discloses a pharmaceutical composition containing *Lonicera caerulea L.* var. *edulis* extract for the prevention and treatment of liver disease, in which the composition exhibits prophylactic and therapeutic effects on liver cancer, hepatocirrhosis, and fatty liver, and Korean Patent No. 10-0454150 discloses an anti-irritant cosmetic composition including 0.001~10% by weight of one or more herbal extracts selected from the group consisting of *Corydalis turtschaminovii, Cynanchum paniculatum,* and *Lonicera caerulea L.* var. *edulis*, based on the total weight of the composition, in which it can be used for the prevention of itching with fewer side effects such as skin rash or skin allergy. However, there have been no inventions regarding the use of a fruit extract of *Lonicera caerulea L.* var. *edulis* in ischemic cerebrovascular disease.

Accordingly, the present inventors have explored substances that can be used for the prevention or treatment of ischaemic cerebral disease, and found that the fruit extract of *Lonicera caerulea L.* var. *edulis* inhibits neurobehavioral impairment and reduces cerebral infarct volume, and thus it can be used as an active ingredient in a prophylactic or therapeutic agent for ischaemic cerebral disease, thereby completing the present invention.

SUMMARY OF THE INVENTION

An objective of the present invention is to provide a pharmaceutical composition containing a fruit extract of *Lonicera caerulea L.* var. *edulis* as an active ingredient for the prevention or treatment of ischemic cerebrovascular disease.

Another objective of the present invention is to provide a health food containing the fruit extract of *Lonicera caerulea L.* var. *edulis* as an active ingredient for the prevention or improvement of ischemic cerebrovascular disease.

Still another objective of the present invention is to provide a method for treating ischemic cerebrovascular disease, including the step of administering to a subject a pharmaceutically effective amount of the fruit extract of *Lonicera caerulea L.* var. *edulis*.

Still another objective of the present invention is to provide a method for protecting nerve cells from oxidative stress, including the step of administering to a subject a pharmaceutically effective amount of the fruit extract of *Lonicera caerulea L.* var. *edulis*.

DETAILED DESCRIPTION OF THE PREFERRED EMBODIMENTS

Figure 1:
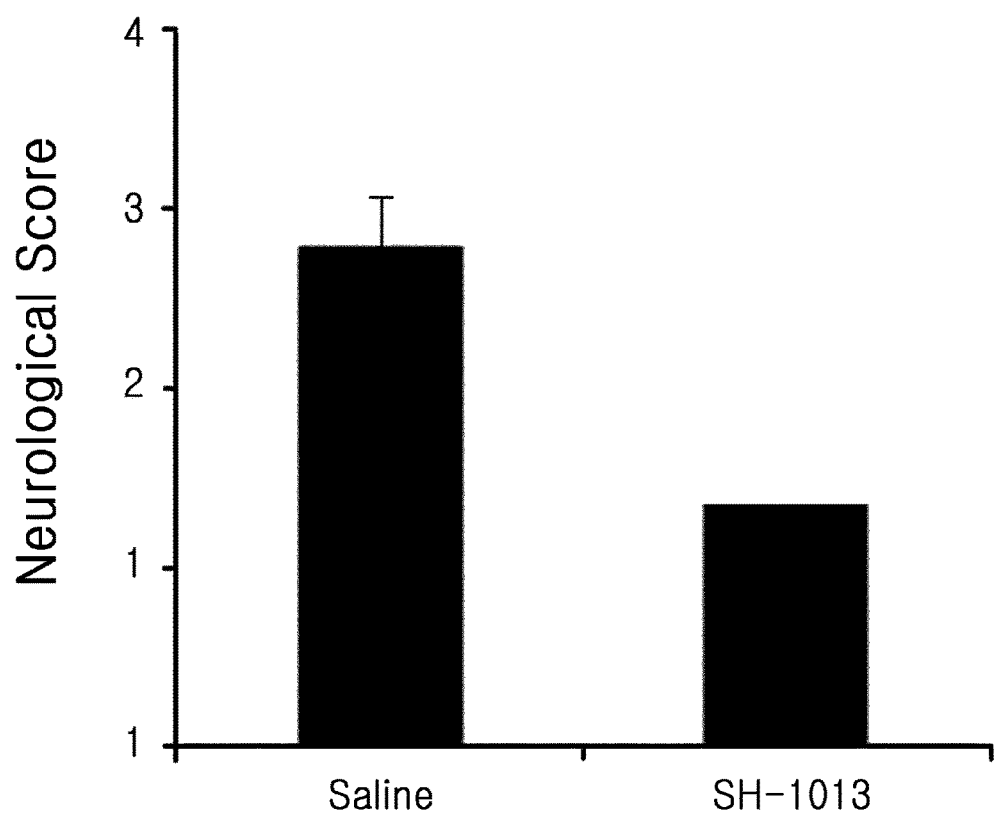
FIG. 1 is a graph showing neurobehavioral scores at 24 hours after inducing ischemia by occlusion of the base part of the middle cerebral artery of a rat for 90 minutes, in which saline indicates a control group, and SH-1013 indicates the fruit extract of *Lonicera caerulea L.* var. *edulis* of the present invention (0, no neurobehavioral impairments (normal); 1, failure to extend left forelimb when the rat was fully lifted by the tail (mild); 2, circling toward the contralateral side of the lesion (moderate); 3, falling toward the contralateral side of the lesion at rest or no spontaneous movement (severe))

Hereinafter, the present invention will be described in detail.

In one aspect to achieve the above objectives, the present invention provides a composition containing a fruit extract of *Lonicera caerulea L.* var. *edulis* as an active ingredient for the prevention and treatment of ischemic cerebrovascular disease.

The term '*Lonicera caerulea L.* var. *edulis*', as used herein, refers to all organs, for example, roots, branches, stems, leaves, flowers and fruits, of natural, hybrid or variant types of *Lonicera caerulea L.* var. *edulis*, but preferably indicates fruits of *Lonicera caerulea L.* var. *edulis*.

The term 'ischemic cerebrovascular disease', as used herein, collectively refers to a disease which occurs when a blood vessel of the brain is blocked for any reason and the blood supply to the brain is interrupted, and it is also called ischemic cerebral disease. The ischemic cerebrovascular disease refers to a disease which occurs when the brain blood flow is reduced and oxygen or glucose becomes depleted to cause nerve cell death of the brain tissue known to be sensitive to cerebral ischemia. The ischemic cerebrovascular disease may include cerebral infarction, stroke, intracerebral hemorrhage, subarachnoid hemorrhage, white matter disorder, vascular dementia or the like.

Preferably, the ischemic cerebrovascular disease of the present invention may be any one selected from the group consisting of vascular dementia, cerebral infarction, stroke, intracerebral hemorrhage, subarachnoid hemorrhage and white matter disorder.

Preferably, the fruit extract of *Lonicera caerulea L.* var. *edulis* of the present invention has the nerve cell-protecting effect, but is not limited thereto.

The term 'extraction', as used herein, refers to a series of processes to obtain an extract, and the term 'extract' refers to a concentrated product resulting from extraction of herbal medicine with a proper extraction solution and evaporation of the extraction solution. The extract may be, but is not limited to, a liquid extract obtained by extraction treatment, a diluted or concentrated liquid of the liquid extract, a dry extract prepared by drying the liquid extract, or a crude purified extract or a purified extract thereof. The extract of the present invention may be prepared by extraction with an extraction solvent or by fractionation with addition of a fractionation solvent to the extract which is prepared by extraction with the extraction solvent. The extraction solvent may be, but is not limited to, water, an organic solvent or a solvent mixture thereof, in which the organic solvent may be C1-C4 alcohols, polar solvents such as ethyl acetate or acetone, non-polar solvents such as hexane or dichloromethane or solvent mixtures thereof. Preferably, the solvent may be water, C1-C4 alcohols or solvent mixtures thereof. The fruit extract of *Lonicera caerulea L.* var. *edulis* may be prepared by general extraction, separation and purification methods known in the art. The extraction method may be, but is not limited to, preferably heating extraction, hot water extraction, cold immersion extraction, reflux cold extraction, or ultrasonic extraction.

The fruit extract of *Lonicera caerulea L.* var. *edulis* of the present invention is preferably prepared by a preparation method including the following steps, but is not limited thereto.

The fruit extract of *Lonicera caerulea L.* var. *edulis* of the present invention may be prepared by a method including the steps of 1) adding alcohol or an alcohol aqueous solution to fruits of *Lonicera caerulea L.* var. *edulis* under stirring, followed by reflux extraction at an extraction temperature of 80 to 100° C. for 3 to 5 hours; 2) separating a filtrate of the solution prepared by reflux extraction of step 1), followed by concentration at 40 to 70° C. under reduced pressure and freeze-drying.

In step 1), the extraction solvent may be water, alcohols or a solvent mixture thereof, preferably, any solvent selected from C1 to C4 lower alcohols or solvent mixtures thereof, 1,3-butylene glycol, but is not limited thereto. Most preferably, extraction is carried out using 1,3-butylene glycol, but is not limited thereto. Most preferably, the extracting solvent is 1 to 100% ethyl alcohol or 1 to 100% methyl alcohol, but is not limited thereto.

In step 1), the amount of the extraction solvent is preferably 10% by weight to 40% by weight, more preferably 30% by weight of the dry weight of *Lonicera caerulea L.* var. *edulis* fruit, but is not limited thereto.

In step 1), the extraction temperature is 10° C. to 100° C., but is not limited thereto, preferably 80 to 100° C., and more preferably 90 to 95° C., but is not limited thereto.

In step 1), the extraction time is preferably 1 hour to 7 hours, more preferably 3 hours to 5 hours, but is not limited thereto. Most preferably, the extraction time is 3 hours, but is not limited thereto. In the method according to the present invention, the extraction frequency is preferably 1 to 5 times, but is not limited thereto.

The preparation method of the extract may be a typical extraction method known in the art, that is, a method using an extraction device, such as hot water extraction, immersion extraction, reflux cold extraction, supercritical extraction, subcritical extraction, heating extraction, high pressure extraction or ultrasonic extraction, or a method using an adsorption resin including XAD and HP-20, preferably ultrasonic extraction at low temperature, but is not limited thereto.

The term 'prevention', as used herein, refers to all actions that inhibit or delay ischemic cerebrovascular disease through administration of the extract or the composition containing the extract as an active ingredient. The term 'treatment', as used herein, refers to all actions that restore or beneficially change ischemic cerebrovascular disease through administration of the extract or the composition containing the extract as an active ingredient.

In one embodiment of the present invention, the fruit extract of *Lonicera caerulea L.* var. *edulis* of the present invention was administered to ischemic cerebrovascular disease animal models, in which cerebral ischemia was induced by occlusion at the base of the middle cerebral artery of the rats under anesthesia, and then use thereof in the treatment of ischemic cerebrovascular disease was evaluated.

In one embodiment of the present invention, neurobehavioral impairments of experimental animals were evaluated by neurological score, and as a result, their neurological score was remarkably lower than that of the control group.

In one embodiment of the present invention, the efficacy of the fruit extract of *Lonicera caerulea L.* var. *edulis* of the present invention on infarct volume was evaluated, and as a result, infarct volume was remarkably reduced by treatment of 100 mg/kg of the fruit extract of *Lonicera caerulea L.* var. *edulis*.

Further, in one embodiment of the present invention, its efficacy was assessed by staining the nerve cells. As a result, the fruit extract of *Lonicera caerulea L.* var. *edulis* showed the effect of remarkably inhibiting nerve cell death due to cerebral ischemia, suggesting that the extract has a predominant nerve cell-protecting efficacy.

Therefore, the fruit extract of *Lonicera caerulea L.* var. *edulis* according to the present invention has the nerve cell-protecting effect, thereby remarkably reducing neurobehavioral impairments and infarct volume in ischemic cerebrovascular disease. Accordingly, the present invention provides a composition containing the fruit extract of *Lonicera caerulea L.* var. *edulis* as an active ingredient for the prevention and treatment of ischemic cerebrovascular disease.

In one specific embodiment of the present invention, the extract according to the present invention is an extract from a natural plant and shows no side effect, and has the nerve cell-protecting effect in ischemic cerebrovascular disease animal models, thereby inhibiting neurobehavioral impairments and reducing infarct volume. Therefore, it can be used in a pharmaceutical composition containing the same as an active ingredient for the prevention or treatment of ischemic cerebrovascular disease.

The composition containing the extract of the present invention may include 0.1 to 50% by weight of the extract, based on the total weight of the composition, but is not limited thereto.

The composition of the present invention may further include a proper carrier, excipient and diluent typically used in the preparation of drugs.

The composition according to the present invention may be formulated into oral formulations such as powder, granule, tablet, capsule, suspension, emulsion, syrup, aerosol, etc., external preparation, suppository or sterilized solution for injection according to the typical method. The carrier, excipient and diluent that can be used in the composition of the present invention may be exemplified by lactose, dextrose, sucrose, sorbitol, mannitol, xylitol, erythritol, maltitol, starch, acacia rubber, alginates, gelatin, calcium phosphate, calcium silicate, cellulose, methyl cellulose, amorphous cellulose, polyvinyl pyrrolidone, water, methyl hydroxybenzoate, propyl hydroxybenzoate, talc, magnesium stearate and mineral oil. Formulations can be prepared by using generally used excipients or diluents such as fillers, extenders, binders, wetting agents, disintegrating agents and surfactant. The solid formulations for oral administration may include tablet, pill, powder, granule, capsule, etc., and are prepared by mixing the composition of the present invention with one or more excipients, for example, starch, calcium carbonate, sucrose or lactose, gelatin, etc. In addition to the simple excipients, lubricants, for example, magnesium stearate, talc, etc. may be used. Examples of a liquid preparation for oral administration include a suspension, a liquid for internal use, an emulsion, a syrup, etc., and various excipients such as a wetting agent, a sweetener, a flavor, a preservative, etc. may be contained, in addition to commonly used simple diluents such as water and liquid paraffin. Examples of the preparation for parenteral administration may include an aseptic aqueous solution, a non-aqueous solvent, a suspension, an emulsion, a lyophilized agent, and suppository. As the non-aqueous solvent and suspension, propylene glycol, polyethylene glycol, plant oil such as olive oil, injectable ester such as ethyloleate may be used. As a suppository base, witepsol, macrogol, tween 61, cacao butter, lauric butter, glycerogelatin or the like may be used.

The pharmaceutical composition may be administered orally or parenterally. Parenteral administration is performed by any one of local administration and systemic administration. Systemic administration is more preferred, and intravenous injection is most preferred.

The preferred dosage of the therapeutic composition of the present invention can be properly determined by those skilled in the art to which the present invention pertains, depending on condition and weight, severity of a disease, preparation of a drug, administration route and time. The therapeutic composition of the present invention is preferably administered in an amount of 0.0001 to 1000 mg/kg per day, and more preferably 0.01 to 100 mg/kg per day for better effect, based on the amount of the fruit extract of *Lonicera caerulea L.* var. *edulis*. The administration frequency can be once a day or a few times a day. The above administration dosage and administration frequency cannot limit the scope of the invention in any way.

The pharmaceutical composition containing the fruit extract of *Lonicera caerulea L.* var. *edulis* of the present invention as an active ingredient for the prevention and treatment of ischemic cerebrovascular disease may be administered to a patient in a single dose by a bolus type or infusion for a relatively short time, or in a multiple dose by fractionated treatment protocol for a long period of time. With respect to the administration concentration of the pharmaceutical composition of the present invention, the effective administration dose for a patient is determined, considering various factors such as age and health conditions of the patient as well as administration route of the drug and treatment frequency. Therefore, considering the factors, those skilled in the art can properly determine the effective administration dose.

The composition of the present invention may further include nutrients, vitamins, electrolytes, flavoring agents, coloring agents, thickeners, pectic acid and its salts, alginic acid and its salts, organic acids, protective colloidal thickeners, pH regulators, stabilizers, antiseptics, glycerin, alcohol, carbonating agents used in carbonated beverages, etc., in addition to the fruit extract of *Lonicera caerulea L.* var. *edulis*. The composition may further include the ingredients either independently or in combination with others. The content of the additional ingredient may be preferably in the range of 0.1 to 20 parts by weight, based on 100 parts by weight of the fruit extract of *Lonicera caerulea L.* var. *edulis*.

The pharmaceutical composition of the present invention may be formulated into an ampule as a single dosage form or a multidose container using a pharmaceutically acceptable carrier and/or excipient according to the method which can be easily carried out by those skilled in the art to which the present invention pertains. In this regard, the formulations may be used in any type suitable for pharmaceutical preparations, including oral preparations such as powder, granule, tablet, capsule, suspension, emulsion, syrup, aerosol, etc., external preparations such as ointment, cream, etc., suppository or sterilized solution for injection.

In another aspect, the present invention provides a health food containing the fruit extract of *Lonicera caerulea L.* var.

*edulis* as an active ingredient for the prevention or improvement of ischemic cerebrovascular disease.

In the present invention, the fruit extract of *Lonicera caerulea L.* var. *edulis* and ischemic cerebrovascular disease are the same as described above.

In one specific embodiment of the present invention, the extract according to the present invention has the nerve cell-protecting effect in ischemic cerebrovascular disease animal models, thereby inhibiting neurobehavioral impairments and reducing infarct volume, and thus it can be used in a health food containing the same as an active ingredient for the prevention or improvement of ischemic cerebrovascular disease.

The type of the food is not particularly limited. Examples of the food to which the substance can be added may include drinks, meats, sausages, bread, biscuits, rice cakes, chocolates, candies, snacks, cookies, pizza, instant noodles, other noodles, chewing gums, dairy products including ice creams, soups, beverages, alcohol beverages, vitamin complex, etc., and all kinds of health foods commonly accepted.

The fruit extract of *Lonicera caerulea L.* var. *edulis* of the present invention may be added to foods, as it is or together with other food or food ingredient, and properly used according to the typical method. The mixing ratio of the active ingredient may be properly determined by the purpose of use (for prevention or improvement). Generally, the extract may be added to the health food in an amount of 0.1 to 90 parts by weight, based on the total weight of the food. However, if it is administered for a long period of time for the purpose of health and hygiene or for the purpose of health control, its amount may be below the range. Because there is no safety problem, the active ingredient may be also used in the above range.

The functional heath drink composition of the present invention is not limited to any specific composition insofar as it is a liquid containing the above extract as essential ingredients in the indicated proportions. Like ordinary beverages, it may include various sweeteners or natural carbohydrates as additional ingredients. Examples of the natural carbohydrates described above may include general sugars such as monosaccharide, for example, glucose and fructose, disaccharides, for example, maltose and sucrose, polysaccharides, for example, dextrin and cyclodextrin, and sugar alcohols such as xylitol, sorbitol and erythritol. As the sweeteners other than those mentioned above, natural sweeteners (thaumatine, stevia extract (e.g., rebaudioside A), glycyrrhizin), and synthetic sweeteners (saccharin, aspartame, etc.) can be used with advantage. The content of the natural carbohydrate is generally about 1 to 20 g, preferably about 5 to 12 g, per 100 ml of the composition of the invention.

In addition to the above ingredients, the extract of the invention may include various nutrients, vitamins, minerals (electrolytes), flavors such as synthetic flavors and natural flavors, coloring matter and enhancer (cheese, chocolate, etc.), pectic acid and its salts, alginic acid and its salts, organic acids, protective colloid thickeners, pH regulators, stabilizers, preservatives, glycerins, alcohols, and carbonating agents for carbonated beverage use. In addition, the extract of the present invention may include natural fruit juices and fruit pulps for the provision of fruit juice drinks and vegetable drinks. These ingredients can be used independently or in combination. The content of these additives is not so critical but can be generally selected from the range of 0.1 to about 20 parts by weight per 100 parts by weight of the extract of the present invention.

In still another aspect, the present invention provides a method for preventing or treating ischemic cerebrovascular disease, including the step of administering to a subject the composition containing a pharmaceutically effective amount of the fruit extract of *Lonicera caerulea L.* var. *edulis* as an active ingredient.

The term 'administration', as used herein, refers to introduction of a predetermined material into a patient in a suitable manner. The administration route of the composition is not particularly limited. As long as it allows the composition to reach a target in the body, any administration route may be taken. Examples of the administration route include intraperitoneal, intravenous, intramuscular, subcutaneous, intradermal, oral, local, intranasal, intrapulmonary and intrarectal administration. However, since peptides are digested upon oral administration, the active ingredient of a composition for oral administration should be coated or formulated for protection against degradation in the stomach.

In still another aspect, the present invention provides a method for protecting nerve cells from oxidative stress, including the step of administering to a subject the composition containing a pharmaceutically effective amount of the fruit extract of *Lonicera caerulea L.* var. *edulis* as an active ingredient.

The term 'oxidative stress', as used herein, refers to a disturbance in the balance between production and elimination systems of reactive oxygen, which is caused by various factors such as chemicals, radiation, ischemia, etc. Bacteria have a group of enzymes induced by reactive oxygen, which are caused by activation of transcription factors due to direct oxidation. In higher organisms, many genes are also induced by oxidative stress, which is considered to be caused by activation of intracellular signal transduction pathways.

Consequently, oxidative stress also induces pathological conditions such as cell injury (particularly, oxidation of cell membrane lipids), mutations due to DNA modification, induction of apoptosis or necrosis, etc.

The oxidative stress can be caused by reactive oxygen species or reactive nitrogen species. The reactive oxygen species indicates superoxide ($O^{2-}$), hydrogen peroxide ($H_2O_2$), hydroxyl radical (OH), and singlet oxygen ($^1O_2$) which are produced by stepwise reduction of triplet oxygen ($^3O_2$), and the reactive nitrogen species includes nitric oxide radical (NO), and peroxy nitrite (ONOO), etc.

In still another aspect, the present invention provides use of the fruit extract of *Lonicera caerulea L.* var. *edulis* in the preparation of a prophylactic or therapeutic agent for ischemic cerebrovascular disease.

In the present invention, the fruit extract of *Lonicera caerulea L.* var. *edulis* and ischemic cerebrovascular disease are the same as described above.

Hereinafter, the present invention will be described in detail with reference to Examples, Experimental Examples, and Preparation Examples.

However, the following Examples, Experimental Examples, and Preparation Examples are for illustrative purposes only, and the invention is not intended to be limited by these Examples, Experimental Examples, and Preparation Examples.

<Example 1> Preparation of Fruit Extract of *Lonicera caerulea L.* var. *edulis*

<1-1> Hot Water Extraction Using Water Solvent

Fruits of the wild *Lonicera caerulea L.* var. *edulis* personally harvested in Yanbian, China and Baekdu Mountain were dried and used in the preparation of a fruit extract of *Lonicera caerulea L.* var. *edulis*. 100 g of *Lonicera caerulea L.* var. *edulis* fruit pulverized was added to 1 liter of distilled water, and stirred well, followed by reflux extraction at an extraction temperature of 90 to 95° C. for 3 hours. Then, a filtrate was separated and the herbal extract was concentrated under reduced pressure at 55~65° C. and then freeze-dried to obtain 21.2 g of an herbal medicine powder extract.

<1-2> Hot Water Extraction Using Water-Alcohol Solvent Mixture 1 liter of 25% ethyl alcohol was added to 100 g of *Lonicera caerulea L.* var. *edulis* fruit which was pulverized as in Example 1-1, and stirred well, followed by reflux extraction for 3 hours at an extraction temperature of 80 to 90° C. which was maintained by heating. Then, a filtrate was separated and the herbal extract was concentrated under reduced pressure at 55~65° C. and then freeze-dried to obtain 19.5 g of an herbal medicine powder extract.

<Example 2> Preparation of Focal Ischemic Model

Sprague-Dawley (SD) rats (250-300 g) were used as an experimental animal. SD rats were fasted for 24 hours, and then anesthetized with 2.5% isoflurane using a gas mix of nitrogen and oxygen at a ratio of 7:3. The common carotid artery and the external carotid artery were ligated, a 17 mm long probe was inserted into the internal carotid artery from the bifurcation point of the internal carotid artery to occlude the base part of the middle cerebral artery for 90 minutes for induction of ischemia. During the induction of ischemia, a rectal thermometer was inserted and the temperature was monitored and maintained at a normal body temperature of 37±0.3° C. After the middle cerebral artery was occluded for a predetermined time, the probe inserted into the internal carotid artery was pulled out to perform reperfusion.

<Example 3> Assessment of Ischemic Brain Injury

<3-1> 2,3,5-Triphenyltetrazolium Chloride (TTC) Staining

To primarily observe the brain tissue injury induced by transient cerebral ischemia, TTC staining was carried out. The brain was removed from the experimental group, and 2-mm thick slices were prepared using a brain matrix and stained with 2% 2,3,5-Triphenyltetrazolium chloride (TTC) solution at 37° C. for 60 minutes. The brain slices stained with the TTC solution were fixed in a 10% neutral buffered formalin solution to measure the infarct volume (Lee et al., Glia, 50:168-181, 2005).

<3-2> Histological Staining

After ischemia, the normal group and each of the experimental groups were injected intraperitonealy with chloral hydrate (400 mg/) at a predetermined time point for general anesthesia. The chest of the experimental animal was opened, and a cannula was inserted into the ascending aorta through the left ventricle. While the animal was exsanguinated through the right ventricle, perfusion washing was performed using an injector (Cole Parmer, USA) with physiological saline (pH 7.4) at a rate of 10 ml per min. Subsequently, the animal was fixed by perfusion with 4% paraformaldehyde (0.1 M phosphate buffer (PB), pH 7.4, and then the skull was broken using a bone cutter to remove the brain therefrom. The fixed brain tissues were embedded in paraffin through a typical tissue treatment procedure, and then 5 μm thick paraffin serial sections were prepared using a microtome (Reichert-Jung, Germany). After deparaffination with xylene, the sections were treated with 100%, 95%, 90, 80%, 70, and 50% ethanol, followed by cresyl violet and acid fuchsin staining to examine distribution and deformation of normal cells. After typical dehydration and clearance processes, the sections were sealed with permount.

<Experimental Example 1> Analysis of Neurobehavioral Observation Score

At 3 hours after induction of cerebral ischemia, SD rats after surgery were observed for neurobehavioral impairments. Neurobehavioral test was scored by fully lifting rats by the tail in the air, by lifting rats by the tail until left hemiplegia occurs, or by examining whether spontaneous left circling occurs. The neurological score was as follows: 0, no neurobehavioral impairments (normal); 1, failure to extend left forelimb when fully lifted by tail (mild); 2, circling toward the contralateral side of the lesion (moderate); 3, falling toward the contralateral side of the lesion at rest or no spontaneous movement (severe).

At about 30 minutes and 3 hours after induction of cerebral ischemia, it was examined whether counterclockwise circling occurs when rats were fully lifted by the tail. Counterclockwise circling was observed in 95 or more of the rats, and neurological score was 2.8±0.28. In contrast, spontaneous circling was reduced in the group treated with the fruit extract of *Lonicera caerulea L.* var. *edulis*, and neurological score was 1.48±0.23 in the group (SH-1013) (100 mg/kg) treated with the fruit extract of *Lonicera caerulea L.* var. *edulis*, indicating significant inhibition of neurobehavioral impairments (FIG. 1).

These results suggest that the fruit extract of *Lonicera caerulea L.* var. *edulis* of the present invention remarkably reduces neurobehavioral impairments in ischemic cerebrovascular disease animal models.

<Experimental Example 2> Ischemic Brain Injury-Protecting Effect of Drug

Figure 2:
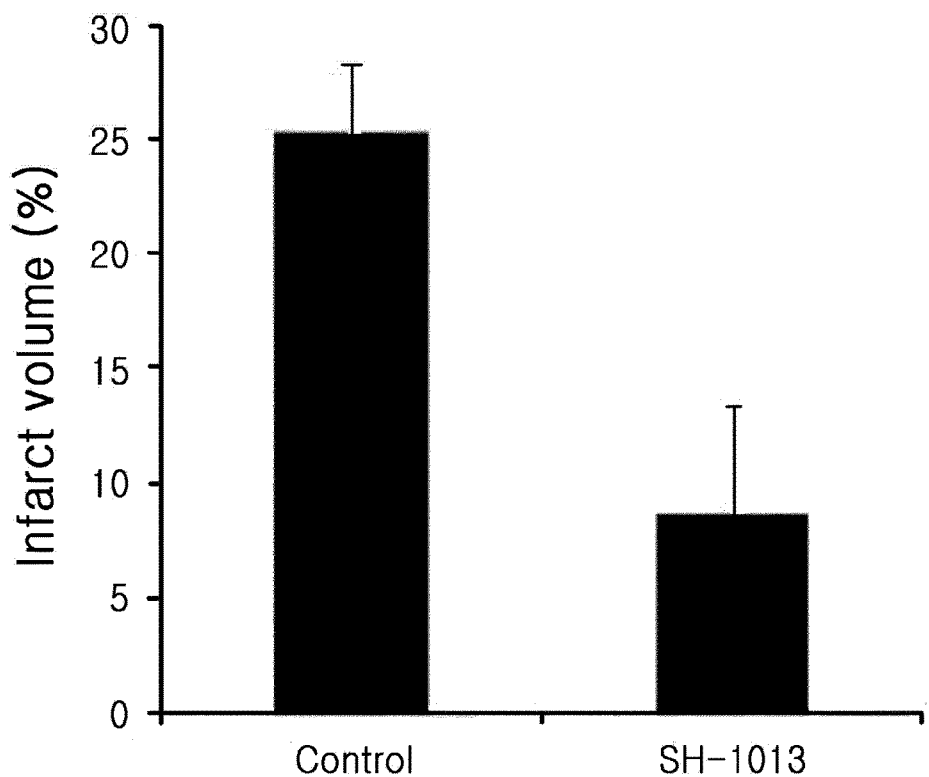
FIG. 2 is a graph showing the effect of the fruit extract of *Lonicera caerulea L.* var. *edulis* of the present invention on the infarct volume in MCAO (middle cerebral artery occlusion)
Figure 3:
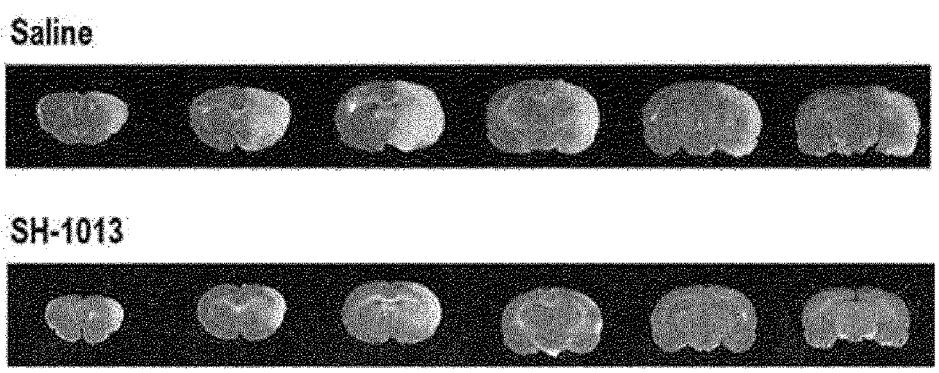
FIG. 3 is a representative TTC-stained tissue image showing the effect of the fruit extract of *Lonicera caerulea L.* var. *edulis* of the present invention on the infarct volume in MCAO (middle cerebral artery occlusion), in which with respect to each experimental group, 6 sections (2 mm-thick) were prepared by cutting the vertex from the frontal pole ranging from 4 mm to 16 mm.

To primarily evaluate the brain injury due to transient MCAO (middle cerebral artery occlusion), TTC staining was carried out and total infarct volume was measured. Normal tissue is stained dark red due to reduction of TTC by mitochondrial enzymes, whereas infarcted tissue is distinguished from the normal tissue due to loss of reduction by mitochondrial damage. 2 mm-thick 6 sections that were serially cut from the anterior region, excluding the olfactory bulbs of the brain of each experimental group, were stained with TTC, and as a result, noticeable infarct areas were observed in Tissue Nos. 2, 3 and 4. The total infarct volume was measured as 25.38±2.85% in the group at 24 hours after ischemia, whereas the total infarct volume (8.59±4.68%) was significantly reduced in the group treated with the fruit extract of *Lonicera caerulea L.* var. *edulis* (SH-1013), indicating that the cerebral infarct volume was reduced by 60% or more in the group treated with the fruit extract of *Lonicera caerulea L.* var. *edulis* (FIGS. 2 and 3).

Figure 4:
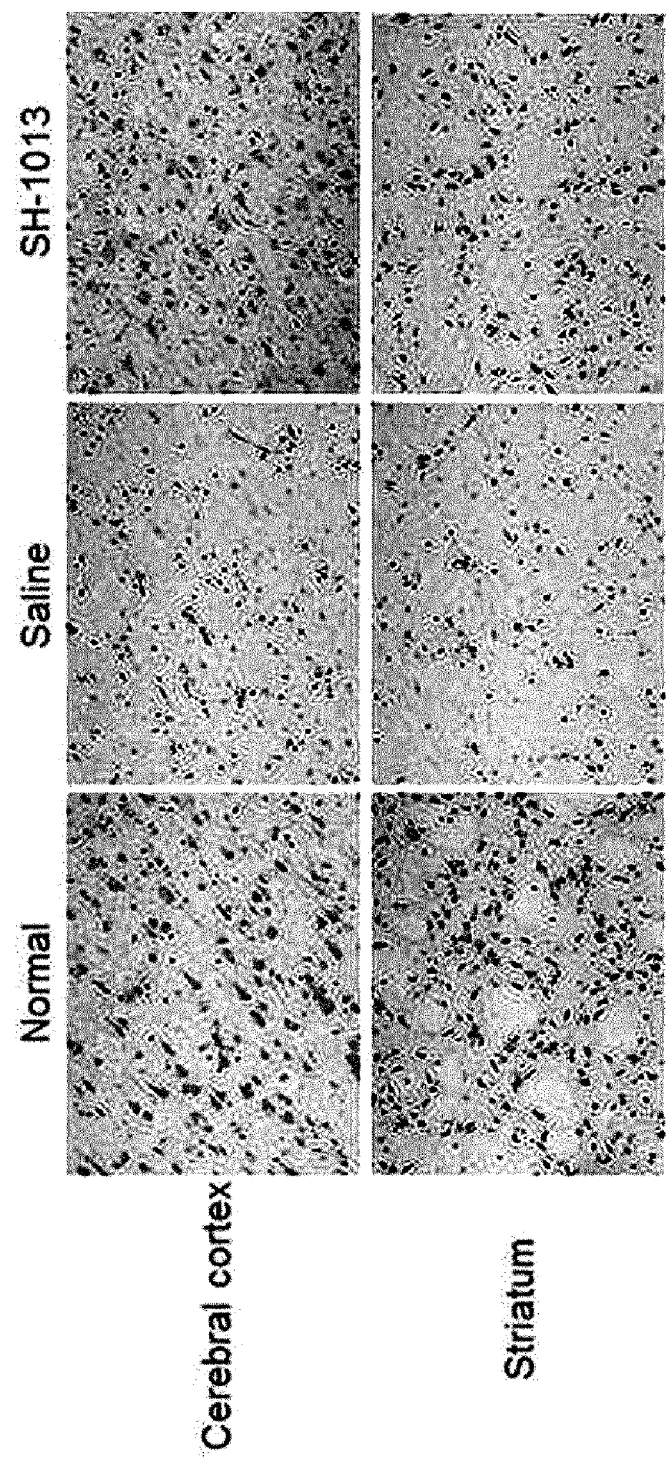
FIG. 4 is a representative cresyl violet-stained tissue image showing the effect of the fruit extract of *Lonicera caerulea L.* var. *edulis* of the present invention on the nerve cell injury in MCAO (middle cerebral artery occlusion), in which cresyl violet-stained, pyramidal-shaped nerve cells were observed in the cerebral, cortex and striatum of each experimental group.

Further, after 2-hr occlusion of middle cerebral artery and 24-hr reperfusion, cresyl violet staining was carried out. As a result, the number of cresyl violet-stained cells was reduced in the ischemic cerebral cortex and ischemic striatum. In particular, no pyramidal-shaped nerve cells were found. In contrast, a large number of pyramidal-shaped nerve cells were observed in the ischemic cerebral cortex and ischemic striatum of the group treated with the fruit extract of *Lonicera caerulea L.* var. *edulis* of the present invention (FIG. 4).

These results suggest that the fruit extract of *Lonicera caerulea* L. var. *edulis* of the present invention remarkably reduces the infarct volume and shows the noticeable nerve cell-protecting effect in ischemic cerebrovascular disease animal models.

<Preparation Example 1> Preparation of Pharmaceutical Formulations

<1-1> Preparation of Powder Formulation

| | |
|---|---|
| Fruit extract of *Lonicera caerulea* L. var. *edulis* | 20 mg |
| Lactose | 20 mg |

The above ingredients were mixed, and then filled into an airtight sac to prepare a powder formulation.

<1-2> Preparation of Tablet Formulation

| | |
|---|---|
| Fruit extract of *Lonicera caerulea* L. var. *edulis* | 10 mg |
| Corn starch | 100 mg |
| Lactose | 100 mg |
| Magnesium stearate | 2 mg |

The above ingredients were mixed, and then tableted according to a typical procedure for tablet preparation to prepare a tablet formulation.

<1-3> Preparation of Capsule Formulation

| | |
|---|---|
| Fruit extract of *Lonicera caerulea* L. var. *edulis* | 10 mg |
| Crystalline cellulose | 3 mg |
| Lactose | 14.8 mg |
| Magnesium stearate | 0.2 mg |

The above ingredients were mixed, and then packed into gelatin capsule according to a typical procedure for capsule preparation to prepare a capsule formulation.

<1-4> Preparation of Liquid Formulation

| | |
|---|---|
| Fruit extract of *Lonicera caerulea* L. var. *edulis* | 20 mg |
| Isomerized sugar | 10 g |
| Mannitol | 5 g |
| Purified water | adequate amount |

Each ingredient was added to and dissolved in purified water according to a typical procedure for liquid formulation, and an adequate amount of lemon flavor was added. Then, the above ingredients were mixed, and purified water was added to a total volume of 100 ml. The resultant was filled into a brown bottle, and sterilized to prepare a liquid formulation.

<1-5> Preparation of Injectable Formulation

| | |
|---|---|
| Fruit extract of *Lonicera caerulea* L. var. *edulis* | 10 µg/ml |
| Dilute hydrochloric acid BP | to pH 7.6 |
| Sodium chloride BP for injection | up to 1 ml |

The fruit extract of *Lonicera caerulea* L. var. *edulis* was dissolved in an adequate volume of sodium chloride EP for injection, and then pH of the resulting solution was adjusted to pH 7.6 using dilute hydrochloric acid BP, and its volume was adjusted using sodium chloride BP for injection, followed by mixing well. The solution was filled into a type I 5 ml-ampoule (clear glass), which was sealed under a headspace of air, by fusion of the glass, and then sterilized by autoclaving at 120° for 15 minutes or longer to prepare an injectable formulation.

<Preparation Example 2> Preparation of Food

Foods containing the fruit extract of *Lonicera caerulea* L. var. *edulis* of the present invention were prepared as follows.
<2-1> Preparation of Wheat Flour Food
0.5~5.0 parts by weight of the fruit extract of *Lonicera caerulea* L. var. *edulis* of the present invention was added to flour and this mixture was used to prepare breads, cakes, cookies, crackers and noodles as foods for health improvement.
<2-2> Preparation of Dairy Products
5~10 parts by weight of the fruit extract of *Lonicera caerulea* L. var. *edulis* of the present invention was added to milk, and the milk was used to prepare a variety of dairy products such as butter and ice cream.
<2-3> Preparation of Health Powdered Food
Brown rice, barley, sweet rice, and adlay were pregelatinized, dried, and then roasted according to a conventionally known method. Then, they were prepared into powders with a size of 60 mesh by using a crusher.

Black soybean, black sesame, and perilla seeds were steamed, dried and then roasted according to a conventionally known method. Then, they were prepared into powders with a size of 60 mesh by using a crusher.

The fruit extract of *Lonicera caerulea* L. var. *edulis* of the present invention was vacuum-concentrated in a vacuum concentrator, and dried by spray and a hot wind dryer. Then, the resulting dried product was prepared into dried powders with a size of 60 mesh by using a crusher.

The grains, the seeds and the dried powders of the fruit extract of *Lonicera caerulea* L. var. *edulis* were blended with each other at the following ratio.

Grains (30 parts by weight of brown rice, 15 parts by weight of adlay, 20 parts by weight of barley), Seeds (7 parts by weight of perilla seeds, 8 parts by weight of black soybean, 7 parts by weight of black sesame), Fruit extract of *Lonicera caerulea* L. var. *edulis* (3 parts by weight),

*ganoderma lucidum* (0.5 parts by weight), and

*rehmannia glutinosa* (0.5 parts by weight).

<2-4> Preparation of Health Care Food

| | |
|---|---|
| Fruit extract of *Lonicera caerulea* L. var. *edulis* | 100 mg |
| Vitamin mixture | adequate amount |
| Vitamin A acetate | 70 µg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 µg |
| Vitamin C | 10 mg |
| Biotin | 10 µg |
| Nicotinic acid amide | 1.7 mg |
| Folic acid | 50 µg |
| Calcium pantothenate | 0.5 mg |
| Inorganic mixture | adequate amount |
| Ferrous sulfate | 1.75 mg |
| zinc oxide | 0.82 mg |
| Magnesium carbonate | 25.3 mg |
| Potassium phosphate monobasic | 15 mg |
| Calcium phosphate dibasic | 55 mg |
| Potassium citrate | 90 mg |
| Calcium carbonate | 100 mg |
| Magnesium chloride | 24.8 mg |

In the above composition containing vitamins and minerals, the ingredients are mixed in a ratio appropriate for a health care food, but the mixing ratio may be changed. The above ingredients were mixed according to a typical procedure for a health care food to prepare granules, which can be used in the preparation of health food compositions according to the conventional method.

<Preparation Example 3> Preparation of Health Care Drink

| | |
|---|---|
| Fruit extract of *Lonicera caerulea* L. var. *edulis* | 100 mg |
| Citric acid | 100 mg |
| Oligosaccharide | 100 mg |
| Plum concentrate | 2 mg |
| Taurine | 100 mg |
| Purified water | to total volume of 500 ml |

The above ingredients were mixed according to a typical procedure for a health care drink, and were heated under stirring for about 1 hour at 85° C. The resultant solution was filtered and fed into a 1 L sterilized container, and the solution was subjected to a sealing and sterilizing process and was kept refrigerated. Then, the final solution was used in preparation of the health care drink composition of the present invention.

In the above composition, the ingredients are mixed in a ratio appropriate for a health care drink, but the mixing ratio may be changed according to regional/national preferences, such as classes, nations, purposes of consumers.

The present invention is not limited to the above described Examples, Experimental Examples and Preparation Examples, and those skilled in the art will appreciate that various modifications and alterations are possible, without departing from the scope and spirit of the invention as disclosed in the accompanying claims.

Effect of the Invention

The fruit extract of *Lonicera caerulea* L. var. *edulis* according to the present invention is an extract from a natural plant and shows fewer side effects, and has the nerve cell-protecting effect in ischemic cerebrovascular disease anima models, thereby inhibiting neurobehavioral impairments and reducing infarct volume. Therefore, a composition containing the same as an active ingredient has excellent prophylactic and therapeutic effects on ischemic cerebrovascular disease.

What is claimed is:

1. A method for treating an ischemic cerebrovascular disease in a subject suffering therefrom, comprising administering to the subject a sufficient amount of a composition containing a pharmaceutically effective amount of a fruit extract of *Lonicera caerulea* L. var. *edulis* as an active ingredient, wherein the fruit extract is an extract obtained by adding pulverized *Lonicera caerulea* L. var. *edulis* to an aqueous or aqueous alcoholic solvent to obtain a mixture; refluxing the mixture at 80° C. to 95° C.; separating a filtrate from the refluxed mixture; concentrating the filtrate under reduced pressure at 55° C. to 65° C. to obtain a concentrate; and freeze-drying the concentrate to obtain the fruit extract of *Lonicera caerulea* L. var. *edulis*.

2. The method according to claim 1, wherein the ischemic cerebrovascular disease is selected from the group consisting of vascular dementia, cerebral infarction, stroke, intracerebral hemorrhage, subarachnoid hemorrhage, and white matter disorder.

* * * * *